(12) United States Patent
Chen et al.

(10) Patent No.: US 8,550,623 B2
(45) Date of Patent: Oct. 8, 2013

(54) COATINGS FOR OPHTHALMIC LENS ELEMENTS

(75) Inventors: Fang Chen, Hallett Cove (AU); Nadine Genevieve Marechal, Gleneig North (AU)

(73) Assignee: Carl Zeiss Vision Australia Holdings, Ltd., Lonsdale (AU)

( * ) Notice: Subject to any disclaimer, the term of this patent is extended or adjusted under 35 U.S.C. 154(b) by 124 days.

(21) Appl. No.: 11/885,343

(22) PCT Filed: Feb. 28, 2006

(86) PCT No.: PCT/AU2006/000243
§ 371 (c)(1),
(2), (4) Date: Oct. 29, 2007

(87) PCT Pub. No.: WO2006/092002
PCT Pub. Date: Sep. 8, 2006

(65) Prior Publication Data
US 2009/0141236 A1    Jun. 4, 2009

(30) Foreign Application Priority Data

Mar. 1, 2005   (AU) ................................. 2005900919

(51) Int. Cl.
*G02C 7/00* (2006.01)
(52) U.S. Cl.
USPC .................................. 351/159.57; 351/159.73
(58) Field of Classification Search
USPC ............ 351/177, 159, 163, 165, 166, 159.01, 351/159.57, 159.73; 427/2.24, 533, 541, 427/162, 164, 165, 168
See application file for complete search history.

(56) References Cited

U.S. PATENT DOCUMENTS

| | | | |
|---|---|---|---|
| 4,544,572 A | 10/1985 | Sandvig et al. | |
| 4,774,035 A | 9/1988 | Carmelite et al. | |
| 4,800,123 A | 1/1989 | Boeckeler | |
| 5,049,321 A | 9/1991 | Galic | |
| 5,079,319 A | 1/1992 | Mueller | |
| 5,096,626 A | 3/1992 | Takamizawa et al. | |
| 5,306,799 A | 4/1994 | Kobayashi et al. | |
| 5,523,030 A | 6/1996 | Kingsbury | |
| 5,531,940 A | 7/1996 | Gupta et al. | |
| 5,608,115 A | 3/1997 | Okazaki et al. | |
| 5,667,735 A | 9/1997 | Bae et al. | |
| 5,733,483 A | 3/1998 | Soane et al. | |
| 5,770,115 A | 6/1998 | Misura | |
| 5,807,975 A | 9/1998 | Amagai et al. | |
| 5,811,503 A | 9/1998 | Herold et al. | |
| 5,851,585 A | 12/1998 | Gupta et al. | |
| 5,880,171 A | 3/1999 | Lim et al. | |
| 5,882,556 A | 3/1999 | Perrott et al. | |
| 5,883,169 A * | 3/1999 | Spector et al. ................ | 524/292 |
| 5,914,174 A | 6/1999 | Gupta et al. | |
| 5,977,276 A | 11/1999 | Toh et al. | |
| 6,109,748 A * | 8/2000 | Spector et al. ................ | 351/159 |
| 6,113,814 A | 9/2000 | Gemert et al. | |
| 6,166,158 A | 12/2000 | Toh et al. | |
| 6,300,464 B2 | 10/2001 | Morijiri et al. | |
| 6,313,251 B1 | 11/2001 | Toh et al. | |
| 6,638,563 B2 * | 10/2003 | McGee et al. ................ | 427/2.24 |
| 6,761,784 B1 * | 7/2004 | Hage ............................. | 156/155 |
| 2002/0076549 A1 | 6/2002 | Welch et al. | |
| 2002/0196408 A1 | 12/2002 | Bhalakia et al. | |
| 2003/0039748 A1 * | 2/2003 | Valint et al. .................... | 427/162 |
| 2003/0203991 A1 | 10/2003 | Schottman et al. | |
| 2004/0096576 A1 * | 5/2004 | Chen ............................ | 427/162 |
| 2004/0125335 A1 | 7/2004 | Vu | |
| 2005/0116381 A1 | 6/2005 | Wong et al. | |
| 2005/0171231 A1 | 8/2005 | Diggins | |
| 2006/0244910 A1 * | 11/2006 | Nam ............................. | 351/166 |
| 2007/0034321 A1 * | 2/2007 | Glacet et al. .................. | 156/230 |
| 2008/0117382 A1 * | 5/2008 | Lacan et al. .................. | 351/166 |
| 2011/0033616 A1 | 2/2011 | Lacan et al. | |

FOREIGN PATENT DOCUMENTS

| | | |
|---|---|---|
| EP | 0102847 B1 | 7/1989 |
| EP | 0 561 507 A1 | 9/1993 |
| EP | 1 392 613 B1 | 3/2004 |
| FR | 2 860 303 A1 | 4/2005 |
| GB | 2096130 A | 10/1982 |
| JP | 2002-103349 A | 4/2002 |
| WO | WO 95/09724 A1 | 4/1995 |
| WO | WO 95/15845 A1 | 6/1995 |
| WO | WO 01/10635 A2 | 2/2001 |
| WO | WO 01/15627 A1 | 3/2001 |
| WO | WO 01/21375 A1 | 3/2001 |
| WO | WO 01/49478 A2 | 7/2001 |
| WO | WO 01/72851 A1 | 10/2001 |
| WO | WO 01/74932 A1 | 10/2001 |
| WO | WO 02/24793 A1 | 3/2002 |
| WO | WO 03/052011 A1 | 6/2003 |
| WO | WO 2005/015270 A1 | 2/2005 |
| WO | WO 2007/128071 A1 | 11/2007 |

* cited by examiner

OTHER PUBLICATIONS

PCT/ISA/210.
PCT/IPEA/409.
International Search Report dated Jun. 18, 2007 from PCT/AU2007/000607.
Annex to the European Search Report corresponding to EP 06 70 4918 dated Dec. 9, 2011.

*Primary Examiner* — Darryl J Collins
(74) *Attorney, Agent, or Firm* — Buchanan Ingersoll & Rooney PC

(57) ABSTRACT

The present disclosure provides a method of forming a removable protective coating on a hydrophobic surface of an ophthalmic lens element. The method includes providing an ophthalmic lens element having a hydrophobic surface. A non-aqueous coating composition is applied so as to coat at least part of the hydrophobic surface. The composition includes a film forming coating polymer and a compatible non-aqueous solvent. A substantial portion of the solvent is removed from the composition to form a removable protective coating on the ophthalmic lens element that adheres to the hydrophobic surface. The disclosure also provides a removable protective coating, and an ophthalmic lens element having the coating.

40 Claims, No Drawings

COATINGS FOR OPHTHALMIC LENS ELEMENTS

This application claims priority from Australian Provisional Patent Application No. 2005900919 filed on 1 Mar. 2005, and the contents of that application are to be taken as incorporated herein by this reference.

FIELD OF THE INVENTION

The present invention relates to removable coatings for ophthalmic lenses and lens blanks ("lens elements"). More particularly, the invention relates to protective coatings for ophthalmic lens elements having a hydrophobic surface. The invention also provides methods for coating ophthalmic lens elements having a hydrophobic topcoat.

BACKGROUND OF THE INVENTION

Ophthalmic lenses are formed from materials such as glass and transparent plastics. Some of the plastics that are used for the manufacture of ophthalmic lenses include thermoplastic polycarbonate and thermoset materials such as CR-39™, Finalite™ (a registered trademark of Sola International Inc.) and Spectralite™ (a registered trademark of Sola International Inc.).

It has become customary to coat ophthalmic lenses with coatings to provide an improvement in properties. For example, abrasion resistant coatings are used to form a hard coating on an ophthalmic lens, whilst anti-reflection coatings including a hydrophobic surface are used to reduce residual reflections. The hydrophobic surface in the latter coatings makes the surface of the anti-reflection coating easier to clean, as it is easier to remove greasy markings or stains such as those caused by touching the lens. A range of ophthalmic lenses having a hard (abrasion resistant) coating, an anti-reflection coating and a hydrophobic topcoat are now available commercially.

Protective coatings are generally used to protect one or more surfaces (or coatings thereon) of a lens during the normal shipping, handling and processing steps that occur after lens manufacture. Usually, once the lens has reached its destination, the protective coating is removed to reveal a lens surface that is relatively unaffected by the shipping, handling and processing steps. Protective coatings can also be used to mask a surface of a lens during post processing steps. For example, there is often a need to carry out further processing steps on the edge of a lens after lens manufacture without affecting the front or back surfaces of the lens. In this case, protective coatings are used to mask the front and/or back surface of the lens to prevent alteration or damage during the edge treatment. An example of an edge treatment where protective coatings may be used is edge coloring wherein a lens edge may need to be coated with a colored coating for aesthetic purposes. During application of the edge coating, the lens surface needs to be protected to prevent inadvertent application of the colored coating material to the optical surface of the lens.

An example of a temporary protective coating is disclosed in French patent application FR2860303, wherein a peelable film is adhered electrostatically to an outer layer of an optical lens. The outer layer is an anti-slip inorganic layer that is mechanically damaged or removed by friction and/or contact. In this case, the inorganic layer provides anti-slip properties to enable the lens to be edged, whilst the peelable film protects the anti-slip layer from inadvertent damage or removal by friction during normal transport and handling.

However, the use of hydrophobic topcoats on ophthalmic lenses has led to problems with the use of protective coatings on lenses. More specifically, there have been difficulties associated with protective coatings not adhering sufficiently to the hydrophobic topcoats, so that the protective properties of the coating may be compromised.

To the best of the Applicant's knowledge there is no removable coating for a hydrophobic surface of a lens element that is robust enough for normal handling of the lens element, and that does not interfere with further processing such as power checks, marking, edging and edge colouring. The present invention aims to provide a coating that overcomes or reduces at least one of the problems with known coatings and processes.

Throughout this specification reference may be made to documents for the purpose of describing various aspects of the invention. However, no admission is made that any reference cited in this specification constitutes prior art. In particular, it will be understood that the reference to any document herein does not constitute an admission that any of these documents forms part of the common general knowledge in the art in any country. The discussion of the references states what their authors assert, and the applicant reserves the right to challenge the accuracy and pertinency of any of the documents cited herein.

SUMMARY OF THE INVENTION

The present invention provides a method of forming a removable protective coating on a hydrophobic surface of an ophthalmic lens element, the method including:
  providing an ophthalmic lens element having a hydrophobic surface;
  applying a non-aqueous coating composition so as to coat at least part of the hydrophobic surface, said composition including a film forming coating polymer and a compatible non-aqueous solvent; and
  removing a substantial portion of the solvent from the composition to form a removable protective coating on the ophthalmic lens element that adheres to the hydrophobic surface.

The present invention also provides an ophthalmic lens element having a hydrophobic surface and a removable protective coating formed from a film forming coating polymer adhered to at least part of the hydrophobic surface.

The present invention also provides a removable protective coating for an ophthalmic lens element having a hydrophobic surface, the coating including a film forming coating polymer that adheres to the hydrophobic surface.

The film forming polymer may be a polymer selected from the list including vinyl polymers, styrene polymers, cellulose polymers and poly(meth)acrylate polymers. Preferred vinyl polymers include poly vinyl acetate, polyvinyl phenol, polyvinyl pyrrolidone, and poly(vinyl pyrolidone co-vinyl acetate). Preferred styrene polymers include polystyrene. Preferred cellulose polymers include ethyl cellulose and hydroxy propyl cellulose. Preferred poly(meth)acrylate polymers include poly(methyl methacrylate) and poly(ethyl methacrylate).

As previously described, there has been a problem in the past with forming coatings on hydrophobic surfaces of ophthalmic lens elements. However, the inventors have now found that it is possible to form a protective coating that adheres sufficiently to a hydrophobic surface of an ophthalmic lens element to allow the lens element to be handled and processed without the protective coating detaching therefrom. The protective coating is robust enough for normal handling, and it does not interfere with further processing steps such as power checks, marking, edging and edge colouring. However, the adhesion of the coating to the hydrophobic surface is also such that the coating can be removed to expose the hydrophobic surface after the further processing steps have been carried out. For example, the protective coating may be removed from the lens element by peeling it away from the surface or washing the lens element with water after the further processing steps have been completed.

The present invention permits a number of processing operations to be carried out on ophthalmic lens elements without the difficulties that have been associated with having a hydrophobic surface on the lens element. For example, the protective coating of the present invention provides an anti-slip surface. Hydrophobic surfaces present difficulties during edging of lenses because the hydrophobic surface tends to make the lens slip when the lens is clamped in an edging machine. However, by forming a protective coating of the present invention on the hydrophobic surface, the adherence between an adhesive pad on a clamping member of the edging machine and the lens surface can be improved significantly.

It has also been discovered that the protective coating of the present invention can be removed from a lens element without removing ink markings on the surface of the lens element. This enables lens elements to be marked for further processing and subsequently overcoated with the protective coating prior to edging. After edging, the protective coating can be removed without significantly affecting the markings.

The protective coating of the present invention can also be used to protect the optical surfaces of lens elements during processing operations that could affect the optical surfaces of the lens elements. For example, in a lens edge colouring process, a lens edge colour material is applied by brushing, rubbing or spraying it onto an edge of a lens. However, the optical surfaces of the lens can easily be marred by any edge colouring material that is inadvertently applied. This is especially a problem when the edge colour material is sprayed onto the edges of the lens because the over-spray can easily contaminate the optical surfaces. When this happens a cleaning step has to be added to clean the lenses. With the protective coating of the present invention, after edging, the lens edge is exposed and the edge colour material can be more readily applied on the edge only. The protective coating can be removed later so that contamination of the optical surfaces can be prevented.

Another example of a use of a removable coating for hydrophobic coated lens element is the protection of a lens element surface, while the second surface is being coated. In a vacuum deposition procedure such as the one used for the application of antireflection lens element surfaces, the first surface of a lens element is coated with the antireflection layers, the lens element is then flipped to expose the uncoated side for coating. During the deposition of the layers on the second side, it is often observed that the surface properties of the coated layers on the first surface of the lens element can be modified. A protective removable coating prevents such an undesirable effect. The protective coating may also be used to prevent surfaces from back spray during vacuum deposition of anti-reflection layers.

GENERAL DESCRIPTION OF THE INVENTION

The present invention, and embodiments thereof, will now be described in more detail. However, before proceeding it is important to note that various terms that will be used throughout the specification have meanings that will be well understood by a skilled addressee. However, for ease of reference, some of these terms will now be defined.

The term "lens element" as used herein refers to a finished or unfinished ophthalmic lens or lens blank manufactured from an optically transparent glass or plastic material. Plastic materials useful in preparation of lens elements are well known in the art and include, by way of example, polycarbonates, polymethacrylates, and the like. The particular plastic material employed is not critical. A 'lens blank' is a lens element that requires some form of treatment, such as cutting a given geometry to deliver a given magnification power, or deposition of a coating. Once all of the cutting and coating steps are completed, the lens blank is termed a 'lens'. The present invention is applicable to both lens blanks and lenses and for the sake of clarity in the following description, the term 'lens element' is used to describe both lenses and lens blanks. However, certain processing operations, such as edging, will normally only be conducted on a lens, whilst other processes, such as coating, will normally only be carried out on lens blank. With that distinction in mind, the terms lens and lens blank are used herein for the purpose of describing the present invention.

The term "hydrophobic surface" refers to a surface having a hydrophobic character. Hydrophobic surfaces of the type referred to herein typically have a contact angle above about 60 degrees using standard tests. Hydrophobic surfaces are usually formed on lens elements by coating at least part of a lens element surface with a hydrophobic coating. Hydrophobic coatings that are known in the art and are typically formed from silane and silazane based compounds having fluorocarbon, perfluorocarbon, polyfluorocarbon, fluoropolyether, or perfluoropolyether groups. Methods for forming hydrophobic coatings are described, for example, in U.S. Pat. No. 6,183,872.

The term "polymer" refers to homopolymers, which are formed from the same type of monomeric units, or copolymers, which are formed from two or more different types of monomeric units.

The term "adheres" refers to a component sticking to a substrate to a degree that permits the substrate to undergo normal handling and processing operations without the component detaching from the substrate. For the purposes of the present invention, a coating can be said to adhere to a hydrophobic surface if the coating does not detach from a lens surface during handling, transportation and/or edging. This may be tested by subjecting a lens element to conditions that replicate normal processing, handling and transport conditions for the lens element.

As discussed, the present invention provides a method of forming a removable protective coating on a hydrophobic surface of an ophthalmic lens element, the method including:
  providing an ophthalmic lens element having a hydrophobic surface;
  applying a non-aqueous coating composition so as to coat at least part of the hydrophobic surface, said composition including a film forming coating polymer and a compatible non-aqueous solvent; and
  removing a substantial portion of the solvent from the composition to form a removable protective coating on the ophthalmic lens element that adheres to the hydrophobic surface.

The present invention also provides an ophthalmic lens element having a hydrophobic surface and a removable protective coating formed from a film forming coating polymer adhered to at least part of the hydrophobic surface.

The present invention also provides a removable protective coating for an ophthalmic lens element having a hydrophobic surface, the coating including a film forming coating polymer that adheres to the hydrophobic surface.

The ophthalmic lens element may be of any type intended for any purpose. This includes lens elements with or without optical corrections. The ophthalmic lens element may be a single integral body ophthalmic lens element or a laminated ophthalmic lens element fabricated by bonding two lens wafers together in a suitable manner, such as by use of a transparent adhesive.

The ophthalmic lens element may have a functional coating on one or more optical surfaces. Functional coatings include abrasion resistant coatings, anti-reflection coatings, anti-static coatings, photochromic layers or coatings, polarized layers or coatings, interference coats, impact primer layers, adhesion primer layers, UV cut-off layers, and the like. The functional coating may be a multi-layer coating. For example, the functional coating may be an anti-reflection coating having from 2 to 12 layers. Typically, the functional coating will have a hydrophobic topcoat layer, which will be the outermost layer and hence will form a hydrophobic surface on the lens element.

The hydrophobic surface may be on any part of the lens element. Typically, the hydrophobic surface will be on both the convex and concave optical surfaces of the ophthalmic lens element. The hydrophobic surface generally will cover substantially all of the optical surface. However, it is possible that the hydrophobic surface may not cover all of the optical surface of the lens element and, in that case, the protective coating of the present invention will cover at least part of the hydrophobic surface.

Hydrophobic surfaces may be prepared from silane and silazane based compounds having fluorocarbon, perfluorocarbon, polyfluorocarbon, fluoropolyether, or perfluoropolyether groups. Typically, hydrophobic coatings are formed by evaporation under vacuum or liquid application using standard dip or spin coating techniques. Methods for forming hydrophobic coatings are described, for example, in U.S. Pat. No. 6,183,872.

The film forming coating polymer may be any polymer that can be coated onto a hydrophobic surface and form a coating layer that has relatively strong adhesion to the hydrophobic surface. By their nature, hydrophobic surfaces have relatively low surface energy and therefore it is difficult to adhere a coating onto such a surface. The adhesion between the polymer coating and the hydrophobic surface is therefore important. If the adhesion of the protective coating with the hydrophobic surface is too weak the coating will be easily peeled off, torn off or detached from the lens element during the transport, handling and/or further processing. Therefore the protective coating has to have sufficient adhesion with the hydrophobic surface of the lens element.

However, it is also desirable for the protective coating to be removable from a lens element after the transport, handling and/or lens processing steps have been carried out. This means that the coating must adhere to the hydrophobic surface sufficiently for the coating to stay on the lens element during handling, transport and/or processing, but the adhesion must also be such that the protective coating can be peeled away from or otherwise removed from the lens element if necessary without substantially altering the properties of the surface of the lens element.

The film forming coating polymer forms the bulk of the protective coating and provides the adhesive properties of the coating. The film forming coating polymer may be present in an amount of about 1% to about 30% (w/w) in the coating composition. In practice, the suitability of any particular polymer may be determined empirically and the person skilled in the art will recognize that certain classes of polymer materials will be more suitable than others for forming the coating layer. The film forming coating polymer may be a homopolymer, a copolymers or mixture of polymers.

Vinyl polymers, styrene polymers, cellulose polymers and poly(meth)acrylate polymers have been found suitable for forming protective coatings. Preferred vinyl polymers include poly vinyl acetate, polyvinyl phenol, polyvinyl pyrrolidone, and poly(vinyl pyrrolidone co-vinyl acetate). Preferred styrene polymers include polystyrene. Preferred cellulose polymers include ethyl cellulose and hydroxy propyl cellulose. Preferred poly(meth)acrylate polymers include poly(methyl methacrylate) and poly(ethyl methacrylate). However, the person skilled in the art will appreciate that there are a large number of poly(meth)acrylate polymers available and some of these may be used to form removable coating according to the present invention. As used herein the term "(meth)acrylate" means either an acrylate group or a methacrylate group.

Some polar hydrophilic polymers that have a strong adhesion with hydrophobic surfaces include polyvinyl pyrrolidone, poly(vinyl pyrrolidone co-vinyl acetate) and polyvinyl phenol. These polymers are able to form films with sufficient adhesion to a hydrophobic surface. In contrast, some hydrophobic polymers, like polystyrene and polyvinyl chloride have weak adhesion with a hydrophobic surface. By blending solutions of the polymers with weak adhesion with the solution of polymers with strong adhesion, sufficient adhesion of polymer coating with the hydrophobic surface can be achieved.

The presence of hydrophilic groups in the polymer can facilitate the protection of ink markings on the surface of lens elements. In most cases, coatings formed from polymers with strong adhesion with a hydrophobic lens surface will remove ink marks when the film is peeled off the lens elements. However, the hydrophilic polymers described herein can be easily wetted by water, and the wetted protective coating can be easily removed by peeling, in which case the ink marks will not be removed.

The solvent is a non-aqueous solvent that is chosen so as to be compatible with the hydrophobic surface and also with the film forming coating polymer. It is relatively difficult to form a film on a hydrophobic surface. Aqueous polymer systems like polyvinyl alcohol in water and aqueous polymer emulsions will not form a film on a hydrophobic surface. However, the present inventors have found that uniform films can be formed on hydrophobic surfaces using polymers dissolved in organic solvents. It will be appreciated that there may be problems with a protective coating that is not formed from a relatively uniform film. Thus, the compatible solvent may be any non-aqueous solvent in which the coating polymer is soluble and which does not have a detrimental effect on the substrate material. Suitable solvents may be selected from the group consisting of lower alkyl alcohols (e.g. methanol, ethanol, n-propranol, i-propanol, n-butanol, sec-butanol, t-butanol etc), ketones (e.g. acetone, butanone, etc), esters (e.g. ethyl acetate, methyl acetate, amyl acetate, butyl acetate etc.), and hydrocarbon solvents, more especially aromatic hydrocarbon solvents (e.g. toluene, xylene etc). Specific solvents that are suitable for this purpose include methanol, ethanol, ethyl acetate, amyl acetate, butyl acetate, acetone, toluene, and compatible mixtures thereof.

In a preferred form of the invention, the non-aqueous coating composition is selected from one of the compositions listed in Table 1 or Table 2.

TABLE 1

Polymer solutions that can be used to form polymer films on hydrophobic surfaces

| Polymer | Solvent | | Polymer concentration (w/w) |
|---|---|---|---|
| Poly vinyl acetate | Mw = 12,800 | Ethyl acetate | 10% |
| Poly vinyl acetate | Mw = 12,800 | Ethyl acetate | 15% |
| Poly vinyl acetate | Mw = 12,800 | Ethyl acetate | 20% |
| Poly vinyl acetate | Mw = 83,000 | Ethyl acetate | 10% |
| Poly vinyl acetate | Mw = 83,000 | Ethyl acetate | 15% |
| Poly vinyl acetate | Mw = 83,000 | Ethyl acetate | 30% |
| Poly styrene | Mw = 280,000 | Ethyl acetate | 10% |
| Poly styrene | Mw = 280,000 | Ethyl acetate | 5% |
| Poly styrene | Mw = 280,000 | Ethyl acetate | 1% |
| Polyvinyl phenol | Mw = 20,000 | Ethyl acetate | 10% |
| Polyvinyl phenol | Mw = 20,000 | Ethanol | 10% |
| Polyvinyl phenol | Mw = 20,000 | Ethanol | 20% |
| Polyvinyl pyrrolidone | Mw = 29,000 | Ethanol | 1% |
| Ethyl cellulose | 46% ethoxy content | Ethyl acetate | 5% |
| Ethyl cellulose | 46% ethoxy content | Toluene | 5% |
| Hydroxy propyl cellulose | Mw = 1,000,000 | Ethanol | 10% |
| Poly(vinyl pyrolidone co-vinyl acetate) | 1.3:1, Mw = 50,000 | Ethanol | 10% |
| Poly(vinyl pyrolidone co-vinyl acetate) | 1.3:1, Mw = 50,000 | Ethanol | 15% |
| Poly(vinyl pyrolidone co-vinyl acetate) | 1.3:1, Mw = 50,000 | Ethanol | 20% |
| Poly (methyl methacrylate) | Mw = 996000 | Ethyl acetate | 5% |
| Poly (ethyl methacrylate) | Mw = 515000 | Ethyl acetate | 10% |

TABLE 2

Solutions of mixed polymers that can be used to form films on hydrophobic surfaces

| Polymer | Polymer | Solvent | Solvent |
|---|---|---|---|
| Poly vinyl pyrrolidone (5%) | Poly vinyl acetate (5%) | Methanol(90%) | |
| Poly vinyl acetate (5%) | Polystyrene(5%) | Ethyl acetate(90%) | |
| Poly vinyl acetate (8%) | Polystyrene(2%) | Ethyl acetate(90%) | |
| Poly vinyl acetate, low molecular weight (20%) | Poly(vinyl pyrolidone co-vinyl acetate) 1.3:1 Mw = 50,000 (2%) | Acetone(78%) | |
| Poly vinyl acetate, low molecular weight (20%) | Poly(vinyl pyrolidone co-vinyl acetate) 1.3:1, Mw = 50,000 (4%) | Acetone(76%) | |
| Poly vinyl acetate, low molecular weight (20%) | Poly(vinyl pyrolidone co-vinyl acetate) 1.3:1, Mw = 50,000 (6%) | Acetone(74%) | |
| Poly vinyl acetate, low molecular weight (15%) | Poly(vinyl pyrolidone co-vinyl acetate) 1.3:1, Mw = 50,000 (0.5%) | Ethyl acetate(75%) | Ethanol(9.5%) |
| Poly vinyl acetate, low molecular weight (15%) | Poly(vinyl pyrolidone co-vinyl acetate) 1.3:1, Mw = 50,000 (1%) | Ethyl acetate(74%) | Ethanol(10%) |
| Poly vinyl acetate, low molecular weight (20%) | Poly(vinyl pyrolidone co-vinyl acetate) 1.3:1, Mw = 50,000 (2%) | Ethyl acetate(65%) | Ethanol(13%) |

TABLE 2-continued

Solutions of mixed polymers that can be used
to form films on hydrophobic surfaces

| Polymer | Polymer | Solvent | Solvent |
|---|---|---|---|
| Poly vinyl acetate, low molecular weight (20%) | Poly(vinyl pyrolidone co-vinyl acetate) 1.3:1, Mw = 50,000 (4%) | Ethyl acetate(64%) | Ethanol(12%) |
| Poly vinyl acetate, low molecular weight (20%) | Poly(vinyl pyrolidone co-vinyl acetate) 1.3:1, Mw = 50,000 (6%) | Ethyl acetate(63%) | Ethanol(11%) |

The coating composition will normally be applied so as to provide a substantially uniform application of the coating composition onto the surface of the ophthalmic lens element. The coating composition can be applied by any suitable means, including spin coating, painting, roll coating, spraying and dip coating. After coating the composition onto the surface of the ophthalmic lens element that contains the hydrophobic surface, the coating is dried to remove most of the solvent from the coating composition. In this way, a coating is formed which remains attached until it is peeled off and the ophthalmic lens element is ready for further processing.

The coating composition prepared as above may be applied to at least one surface of a lens element. If the protective coating is used as an anti-slip coating, the coating composition will be applied to the convex surface only or to both surfaces of a lens which are in contact with a clamping member of an edging machine. For ease of application, the coating will generally be applied so that it is coextensive with the surface of the lens element. However, it may not be necessary for the coating to cover the whole of the surface of the lens element and, for example, it may be sufficient to coat only that part of the surface of a lens that will be in abutment with the clamping member when a lens is being edged.

Sufficient amounts of the coating composition are applied onto the surface or surfaces of the ophthalmic lens element to provide for a coating thickness, after solvent removal, of about 1 micron to about 20 microns.

The coating composition can optionally contain additives such as plasticisers. Plasticisers may be used to improve coating flexibility and peelability. Suitable plasticisers include, by way of example, dipropylene glycol dibenzoate, butyl benzyl phthalate, diethylene glycol dibenzoate, and the like.

After the coating composition has been applied a substantial amount of the solvent is removed from the composition so as to form the protective coating in the form of a film on the hydrophobic surface. Typically, the solvent can be removed by drying the coating composition at room temperature or at elevated temperature. The coating composition could also be dried at reduced pressure, if necessary.

After the protective coating has been applied, standard processing operations can be carried out on the lens element. Also, the lens element can be transported and handled in the normal way with physically affecting the hydrophobic surface(s) of the lens element.

As discussed, the protective coating of the present invention may also be used to provide an anti-slip surface, which can assist with the edging of lenses. There have been difficulties with edging and fitting lenses having hydrophobic topcoats in frames. The final stage in the preparation of an ophthalmic lens is an edging or trimming (hereinafter referred to as "edging") step in which an edge or periphery of the lens is machined so that it can mate with a frame into which the lens is to be fitted. The edging step involves securing the lens in the chuck of an edging machine, rotating the lens and then grinding the edge or periphery. Typically, the lens is secured between axial clamping members with one of the clamping members having a double-sided adhesive pad which bears axially on the convex surface towards the centre of the lens, and a support which bears axially on the concave surface of the lens. With lenses having hydrophobic topcoats on the convex side of the lens, the double-sided adhesive pad has to bear against the hydrophobic surface and the poor adhesion of the double-sided adhesive pad on the slippery lens surface gives rise to a tendency for the lens to slip during the edging process which can result in the lens shape being incorrect and the lens being ruined.

In an attempt to overcome this problem, commercially available adhesive stickers are often applied to the lens surface having the hydrophobic topcoat. The adhesive surface of the sticker usually provides sufficient adhesion to the hydrophobic surface, whilst the opposing surface of the sticker also delivers sufficient adhesion with the double-sided adhesive pad on the clamping member of the edging machine. However, a problem arises with this commonly used technique because adhesion of the stickers can be reduced if they are not handled carefully or if the stickers are used on highly curved lens surfaces because the flat sticker tends to wrinkle when it is placed on the surface. Also, the adhesive used in the sticker is usually hazy and does not allow routine lens power checks to be performed while the sticker is on the lens. Additionally, when the sticker is removed from the lens surface after completion of the edging, ink markings, such as those applied on the lens surface to facilitate the positioning of the edged lenses in the frame, are removed with the sticker.

A further attempt to overcome difficulties with the handling of hydrophobic coated lenses is described in published United States patent application 20030049370 which has been assigned to Essilor International Compagnie General d'Optique. This specification discloses a temporary anti-slip layer that can be applied over hydrophobic topcoats to minimize or prevent slipping during edging. The anti-slip layer is a mineral layer of magnesium fluoride or alumina and praseodyme oxides that is deposited by evaporation in a vacuum treatment chamber in a step immediately following deposition of the hydrophobic layer.

In practice, it has been found that an anti-slip coating that is formed according to the disclosure of United States patent application 20030049370 is difficult to handle as it can be affected by finger marks and it is relatively easy to remove, for instance, by wiping with a dry tissue. This presents problems during handling of the lens because the anti-slip layer can be wiped off accidentally. In practice, this layer also does not deliver the anti-slip benefit on freshly coated lenses. To overcome these issues, a solution has been suggested in International patent application WO2004110946 where an additional process step is added to reduce this effect. However, there may be further processing difficulties with ophthalmic lenses having an anti-slip layer that is formed in accordance with the disclosures of United States patent application 20030049370 and International patent application WO2004110946. Typically, lenses contain markings on a surface to assist in alignment of a lens during further processing to form a prescription lens. The markings are applied to the surface of the lens with ink. In practice, the ink marking would have to be applied before the aforementioned anti-slip layer is applied, but this is not possible as the aforementioned anti-slip layer is applied in vacuum immediately after the hydrophobic layer. If the ink markings are applied after the aforementioned anti-slip layer is applied, the markings will be wiped off with the anti-slip layer.

In addition to the above uses, the protective coating of the present invention can also be used to protect the optical surfaces in a lens edge colouring process.

Using the compositions and methods described herein, it is also possible to form a protective coating that is highly transparent. The transparency of the coating may be important if the operator needs to check refractive properties of the lens, such as the "through power" of the lens with the protective coating in place. More particularly, it has been found that a coating formed from polyvinyl pyrrolidone or poly(vinyl pyrolidone co-vinyl acetate) has very good transparency.

After the transport, handling and/or processing steps have been carried out, the protective coating can be removed. For this reason, the protective coating may be referred to as a temporary coating. The protective coating may be removed by physically peeling the coating from the lens element surface. Alternatively, the presence of hydrophilic polymers in the coating means that the coating can be wetted. After wetting, the coating can be peeled away from the lens element surface, or the coating can be washed off with water.

The protective coating can be removed from a lens element without removing ink markings on the lens element surface. This enables lens elements to be marked for further processing and subsequently overcoated with the protective coating prior to edging. After edging, the protective coating can be removed without affecting the markings.

DESCRIPTION OF PREFERRED EMBODIMENTS

The present invention will now be described in relation to examples of preferred embodiments. However, it must be appreciated that the following description is not to limit the generality of the above description.

Example 1

General Procedure

A coating composition according to any one of the compositions given in Table 1 or Table 2 can be prepared by mixing the polymer component with the solvent in the prescribed amounts.

The coating composition can then be spin coated onto a surface of a lens having a hardcoat, and AR coating and a hydrophobic topcoat. The hydrophobic topcoat may be similar to the one described in U.S. Pat. No. 6,183,872. The coating can then be dried at room temperature to form the protective coating.

The coated lens can then be handled, transported or further processing steps can be carried out, as required.

When necessary, the protective coating can be removed by peeling it from the lens. Alternatively, if the coating is water-soluble it can also be removed by contacting the coating with water.

Example 2

A coating composition comprising 10 parts polyvinylacetate (low molecular weight); 1 part poly(vinylpyrrolidone-co-vinyl acetate); 100 parts ethyl acetate and 7 parts ethanol was prepared by mixing.

The coating composition was then spin coated at 1000 rpm onto the convex surface of CR-39™ lens with hardcoat, AR coating and hydrophobic topcoat. The hydrophobic topcoat was similar to the one described in U.S. Pat. No. 6,183,872. The coating was then dried for 20 seconds at room temperature.

The coated lens could then be edged using typical settings on a suitable edging machine. The clamp pressure and speed settings for the edging step were the same as those used for non-slippery lenses and no slippage of the lens was observed during the edging step.

After edging, the anti-slip coating can be removed by peeling it from the lens. Upon removal of the coating, any ink markings on the surface of the lens were not altered. Alternatively, the coating itself is water-soluble and therefore it can also be removed by contacting the coating with water. The anti-slip coating may be removed automatically in wet edging machines.

Example 3

A coating composition comprising 10 parts polyvinylacetate (low molecular weight); 1 part poly(vinylpyrrolidone-co-vinyl acetate); 100 parts ethyl acetate and 7 parts ethanol was prepared by mixing.

Hard and AR coated polycarbonate lenses with a hydrophobic topcoat similar to the one described in U.S. Pat. No. 6,183,872 were spin coated with above coating solution on both sides. A thin layer polymeric coating was formed on the lenses after drying for 20 seconds at room temperature.

The coated lens was then edged using typical settings on a suitable edging machine. The clamp pressure and speed settings for the edging step were the same as those used for non hydrophobic coated lenses and no slippage of the lens was observed during the edging step.

After edging, the lens edge was sprayed with a UV curable edge colouring coating, then the edge colouring coating was cured by UV light. The over spray of the edge colouring coating on the optical surfaces of the lenses was easily cleaned off the lens by peeling off the protective coating.

Example 4

A coating composition comprising 10 parts polyvinylacetate (low molecular weight); 1 part poly(vinylpyrrolidone-co-vinyl acetate); 100 parts acetone was prepared by stirring for three hours at room temperature.

A CR-39™ lens with hardcoat, AR coating and a hydrophobic topcoat similar to the one described in U.S. Pat. No. 6,183,872 was dipped in the above coating solution for ten seconds, then the lens was pulled out of the solution slowly. A uniform coating was formed on the lens after drying at room temperature for 20 seconds. The coating thickness was about 2 microns.

The coated lens was then edged using typical settings on a suitable edging machine. The clamp pressure and speed settings for the edging step were the same as those used for non-slippery lenses and no slippage of the lens was observed during the edging step.

After edging, the anti-slip coating can be removed by peeling it from the lens. Upon removal of the coating, any ink markings on the surface of the lens were not altered. Alternatively, the coating itself is water-soluble and therefore it can also be removed by contacting the coating with water. The anti-slip coating may be removed automatically in wet edging machines.

Example 5

A multilayer anti-reflection coating including a hydrophobic surface was deposited by evaporation under vacuum on the front surface of two hardcoated CR39™ lenses with an oval shape, held by a spring-clamp on the sectors of the coater's calotte. The first lens was then spin-coated on the front surface with the coating of Example 2. The second lens was not treated.

Both lenses were inserted back in the vacuum chamber, held by a spring-clamp on the sectors of the coater's calotte to coat the concave side of the lenses with the multilayer anti-reflection coating including a hydrophobic surface. After deposition and removal with water of the protective layer on the front surface of the first lens, the hydrophobic properties of the lenses were checked using acetone wettability. The acetone droplets beaded on any point on the front surface of the first lens over the whole area of the surface, indicating it was hydrophobic while the acetone spread on front surface of the second indicating that the second lens surface was not homogenously hydrophobic. Therefore the coating of the invention was effective in protecting the hydrophobic surface of the lens coated with this coating.

Example 6

A protective coating composition comprising 5 parts polyvinylacetate (medium molecular weight) and 50 parts ethyl acetate was prepared by stirring at room temperature for 10 hours The coating composition was then spin coated at 1000 rpm onto the convex surface of CR-39™ lens with hardcoat, AR coating and a hydrophobic topcoat (similar to the one described in U.S. Pat. No. 6,183,872). The coating was then dried for 20 seconds at room temperature.

The coated lens was then edged using typical settings on a suitable edging machine. The clamp pressure and speed settings for the edging step were the same as those used for non hydrophobic coated lenses and no slippage of the lens was observed during the edging step.

After edging, the protective coating could be removed by peeling it from the lens.

Example 7

A protective coating composition comprising 5 parts poly (ethyl methacrylate) (Mw=515000) and 50 parts ethyl acetate was prepared by stirring at room temperature for 10 hours The coating composition was then spin coated at 1000 rpm onto the convex surface of CR-39™ lens with hardcoat, AR coating and a hydrophobic topcoat (similar to the one described in U.S. Pat. No. 6,183,872). The coating was then dried for 20 seconds at room temperature.

Coated lenses were then tested together with the control lenses using standard packaging and transportation conditions. After testing, the protective coating was removed by peeling it from the lens. The lenses were inspected for scratches. We found the lenses having protective coating had less scratches caused by packaging and transportation than the control lenses (without a protective coating).

Example 8

A protective coating composition comprising 2.5 parts poly(methyl methacrylate) (Mw=996000) and 50 parts ethyl acetate was prepared by stirring at room temperature for 10 hours The coating composition was then spin coated at 1000 rpm onto the convex surface of CR-39™ lens with hardcoat, AR coating and a hydrophobic topcoat (similar to the one described in U.S. Pat. No. 6,183,872). The coating was then dried for 20 seconds at room temperature.

The coated lens could was then edged using typical settings on a suitable edging machine. The clamp pressure and speed settings for the edging step were the same as those used for non hydrophobic coated lenses and no slippage of the lens was observed during the edging step.

After edging, the protective coating could be removed by peeling it from the lens.

Finally, it will be appreciated that various modifications and variations of the described compositions, methods and articles of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are apparent to those skilled in the relevant field are intended to be within the scope of the present invention.

The invention claimed is:

1. A removable protective coating for an ophthalmic lens element having a hydrophobic surface covering substantially all of an optical surface of said ophthalmic lens element, wherein the ophthalmic lens element is to be fitted to a frame the coating comprising a film forming coating polymer selected from the group consisting of styrene polymers, cellulose polymers, polyvinyl acetate, polyvinyl phenol, polyvinyl pyrrolidone, and poly (vinyl pyrrolidone co-vinyl acetate) and a compatible non- aqueous solvent, such that the coating adheres to the hydrophobic surface, wherein the protective coating is removable by non-abrasively washing it off with water or non-abrasively physically peeling the coating from the lens element surface optionally after wetting the coating.

2. A removable protective coating according to claim 1, wherein the film forming polymer is selected from the list consisting of styrene polymers and cellulose polymers.

3. A removable protective coating according to claim 1, wherein the film forming coating polymer is selected from the list consisting of polyvinyl acetate, polyvinyl phenol, polyvinyl pyrrolidone, and poly (vinyl pyrrolidone co-vinyl acetate).

4. A removable protective coating according to claim 1, wherein the styrene polymer is polystyrene.

5. A removable protective coating according to claim 1, wherein the cellulose polymer is selected from the list consisting of ethyl cellulose and hydroxy propyl cellulose.

6. A removable protective coating according to claim 1, wherein the coating composition contains film forming coating polymer in an amount of about 1% to about 30% (w/w).

7. A removable protective coating according to claim 1, wherein the film forming coating polymer is a blend of at least one hydrophobic polymer and at least one hydrophilic polymer.

8. A removable protective coating according to claim 7, wherein the hydrophilic polymer is selected from the list consisting of polyvinyl pyrrolidone, polyvinyl pyrolidone co-vinyl acetate) and polyvinyl phenol.

9. A removable protective coating according to claim 7, wherein the hydrophobic polymer is selected from the list consisting of polystyrene and polyvinyl chloride.

10. A removable protective coating according to claim 1, wherein the protective coating further includes an organic solvent.

11. A removable protective coating according to claim 10, wherein the solvent is selected from the list consisting of lower alkyl alcohol, ketone, ester.

12. A removable protective coating according to claim 11, wherein the solvent is selected from the list consisting of methanol, ethanol, ethyl acetate, amyl acetate, butyl acetate, acetone, and compatible mixtures thereof.

13. A removable protective coating according to claim 1, wherein the thickness of the coating is about 1 micron to about 20 microns.

14. A removable protective coating according to claim 1, wherein the adhesion of the protective coating to the hydrophobic surface is such that the protective coating can be removed from the lens element without removing ink markings on the surface of the lens element.

15. A removable protective coating according to claim 1, wherein the removable coating does not interfere with further processing of the lens element.

16. A removable protective coating according to claim 1, wherein the lens element can be handled and processed without the protective coating detaching therefrom.

17. An ophthalmic lens element having a hydrophobic topcoat and a removable protective coating according to claim 1.

18. An ophthalmic lens element according to claim 17, wherein the ophthalmic lens element has a functional coating on one or more optical surfaces.

19. An ophthalmic lens element according to claim 18, wherein the functional coating is selected from the list consisting of abrasion resistant coatings, anti-reflection coatings, anti-static coatings, photochrome coatings, and combinations thereof.

20. A removable protective coating according to claim 1, wherein the protective coating is removable by physically peeling the coating from the lens element surface after wetting the coating.

21. A method of forming a removable protective coating on a hydrophobic surface of an ophthalmic lens element wherein the ophthalmic lens element is to be fitted to a frame, the method comprising:
providing an ophthalmic lens element having a hydrophobic surface covering substantially all of an optical surface of the ophthalmic lens element;
applying a non-aqueous coating composition so as to coat at least part of the hydrophobic surface, said composition including a film forming coating polymer selected from the group consisting of styrene polymers, cellulose polymers, polyvinyl acetate, polyvinyl phenol, polyvinyl pyrrolidone, and poly (vinyl pyrrolidone co-vinyl acetate) and a compatible non-aqueous solvent; and
removing a substantial portion of the solvent from the composition to form a removable protective coating on the ophthalmic lens element that adheres to the hydrophobic surface,
wherein the protective coating is removable by non-abrasively washing the coating off with water or non-abrasively physically peeling the coating from the lens element surface optionally after wetting the coating.

22. A method of forming a removable protective coating according to claim 21, wherein the film forming polymer is selected from the list consisting of styrene polymers and cellulose polymers.

23. A method of forming a removable protective coating according to claim 21, wherein the film forming coating polymer is selected from the list consisting of polyvinyl acetate, polyvinyl phenol, polyvinyl pyrrolidone, and poly (vinyl pyrrolidone co-vinyl acetate).

24. A method of forming a removable protective coating according to claim 21, wherein the styrene polymer is polystyrene.

25. A method of forming a removable protective coating according to claim 21, wherein the cellulose polymer is selected from the group consisting of ethyl cellulose and hydroxy propyl cellulose.

26. A method of forming a removable protective coating according to claim 21, wherein the coating composition contains film forming coating polymer in an amount of about 1% to about 30% (w/w).

27. A method of forming a removable protective coating according to claim 21, wherein the film forming coating polymer is a blend of at least one hydrophobic polymer and at least one hydrophilic polymer.

28. A method of forming a removable protective coating according to claim 27, wherein the hydrophilic polymer is selected from the list consisting of polyvinyl pyrrolidone, polyvinyl pyrolidone co-vinyl acetate) and polyvinyl phenol.

29. A method of forming a removable protective coating according to claim 27, wherein the hydrophobic polymer is selected from the list consisting of polystyrene and polyvinyl chloride.

30. A method of forming a removable protective coating according to claim 21, wherein the solvent is an organic solvent.

31. A method of forming a removable protective coating according to claim 30, wherein the solvent is selected from the list consisting of lower alkyl alcohol, ketone, and ester.

32. A method of forming a removable protective coating according to claim 31, wherein the solvent is selected from the list consisting of methanol, ethanol, ethyl acetate, amyl acetate, butyl acetate, acetone, toluene and compatible mixtures thereof.

33. A method of forming a removable protective coating according to claim 30, wherein the solvent is removed by drying the coating composition at room temperature or at elevated temperature.

34. A method of forming a removable protective coating according to claim 21, wherein the thickness of the coating, after solvent removal, is about 1 micron to about 20 microns.

35. A method of forming a removable protective coating according to claim 21, wherein the adhesion of the protective coating to the hydrophobic surface is such that the protective coating can be removed from the lens element without removing ink markings on the surface of the lens element.

36. A method of forming a removable protective coating according to claim 21, wherein the removable coating does not interfere with further processing of the lens element.

37. A method of forming a removable protective coating according to claim 21, wherein the lens element can be handled and processed without the protective coating detaching therefrom.

38. A removable protective coating on a hydrophobic surface of an ophthalmic lens element produced according to the method of claim 1.

39. An ophthalmic lens element including a removable protective coating produced according to the method of claim 21.

40. A method of forming a removable protective coating according to claim 21, wherein the protective coating is removable by physically peeling the coating from the lens element surface after wetting the coating.

* * * * *